United States Patent [19]

Harwood et al.

[11] 4,399,460

[45] Aug. 16, 1983

[54] VIDEO SIGNAL PEAKING CONTROL SYSTEM WITH PROVISION FOR AUTOMATIC AND MANUAL CONTROL

[75] Inventors: Leopold A. Harwood, Bridgewater, N.J.; Robert L. Shanley, II; James Hettiger, both of Indianapolis, Ind.

[73] Assignee: RCA Corporation, New York, N.Y.

[21] Appl. No.: 310,139

[22] Filed: Oct. 9, 1981

[51] Int. Cl.³ .................. H04N 5/14; H04N 5/52; H03K 1/00

[52] U.S. Cl. ...................... 358/166; 358/37; 330/96

[58] Field of Search ............... 358/37, 17 A, 166, 162, 358/160, 184; 330/96, 132, 254, 279, 288

[56] References Cited

U.S. PATENT DOCUMENTS

| | | | |
|---|---|---|---|
| 4,069,505 | 1/1978 | Burdick et al. | 358/162 |
| 4,075,661 | 2/1978 | Heffron | 358/166 |
| 4,090,217 | 5/1978 | Goyal et al. | 358/37 |
| 4,245,235 | 1/1981 | Lagoni | 358/37 |
| 4,296,435 | 10/1981 | D'Hautecourt et al. | 358/166 |
| 4,351,003 | 9/1981 | Harlan | 358/166 |

OTHER PUBLICATIONS

Schematic Circuit Diagram (FIG. 31, pp. 39-40) for the RCA CTC-111 Color Television Receiver, as Published in the RCA Television Service Data Bulletin (No. C-3, 1981) available from the RCA Consumer Electronics Division, Technical Publications.

*Primary Examiner*—Tommy P. Chin
*Attorney, Agent, or Firm*—Eugene M. Whitacre; Paul J. Rasmussen; Ronald H. Kurdyla

[57] ABSTRACT

A DC coupled system for automatically controlling the high frequency peaking content of a video signal is disclosed. The system includes a DC coupled control path comprising a peak detector for developing a control voltage representative of the high frequency content of the video signal exclusive of video signal DC components, and is preceded by a video signal amplifier. A filter for shaping the frequency response of the control path is connected to the amplifier. A manually adjustable peaking control for controlling the DC bias of the amplifier is also connected to the amplifier. The filter and adjustable peaking control exhibit mutually independent operation, and are both connected to the amplifier via the same single terminal.

12 Claims, 3 Drawing Figures

VIDEO SIGNAL PEAKING CONTROL SYSTEM WITH PROVISION FOR AUTOMATIC AND MANUAL CONTROL

This invention concerns a system for automatically and manually controlling the amount of peaking present in a video signal processed by a television receiver. In particular, the system includes a filter for determining the frequency response of the system and a manually adjustable peaking control, both coupled to the system via the same terminal and arranged to exhibit mutually independent operation.

A reproduced image developed in response to video signals processed by a television receiver can be subjectively improved or enhanced by increasing the slope or "steepness" of video signal amplitude transitions. Such enhancement, commonly referred to as signal "peaking", is typically associated with the high frequency information of the video signal. For example, horizontal image peaking can be achieved by generating a signal "preshoot" just before an amplitude transition, and a signal "overshoot" just after an amplitude transition, so that black-to-white and white-to-black video signal amplitude transitions are accentuated.

The amount of peaking manifested by a video signal processed by a television receiver can vary from one channel to another and can be attributed to a variety of sources. Horizontal peaking can be provided at the broadcast transmitter and by circuits within the television receiver in fixed or controllable amounts. Signal peaking or depeaking can also result from a signal "mismatch" (e.g., due to an impedance mismatch) in a cable television signal distribution path. Since signal peaking accentuates the high frequency response of a video signal, the presence of high frequency noise is also a consideration in determining the amount of peaking to be imparted to a video signal. Accordingly, it is desirable to automatically control the amount of video signal peaking as a function of the high frequency content of a video signal including detail and peaking components imparted from various sources, to optimize the amount of video signal peaking consistent with an objective of providing a reproduced image with good image detail for various signal conditions. For this purpose the frequency response of the control system should be established by means of an appropriate filter network such that the system responds to a prescribed range of high frequency video signals which is considered to represent the peaking content of the video signal.

In a television receiver it is also desirable to provide the viewer with a control (e.g., a potentiometer) for manually adjusting the peaking content of the video signal and thereby the sharpness of a displayed picture.

According to the present invention, the disclosed peaking control system includes a filter for shaping the frequency response of the system, and a manually adjustable peaking control, both of which are connected to the system via the same terminal and exhibit mutually independent operation. When the system is constructed as an integrated circuit, both the filter and the peaking control are connected to the peaking control path of the system by means of the same external terminal of the integrated circuit, thereby conserving the limited number of available external terminals of the integrated circuit.

In accordance with a feature of the invention, the peaking control path includes a DC coupled amplifier comprising an upper rank amplifier transistor responsive to the video signals, and a lower rank transistor which serves as a current source for the amplifier transistor. The filter and the adjustable peaking control are coupled via the single terminal to the output of the current source transistor, at the junction of the amplifier and current source transistors, the latter of which advantageously exhibits a high impedance. In a preferred embodiment the filter comprises a series tuned circuit coupled between the external terminal and a point of reference potential (e.g., ground).

Figure 1:
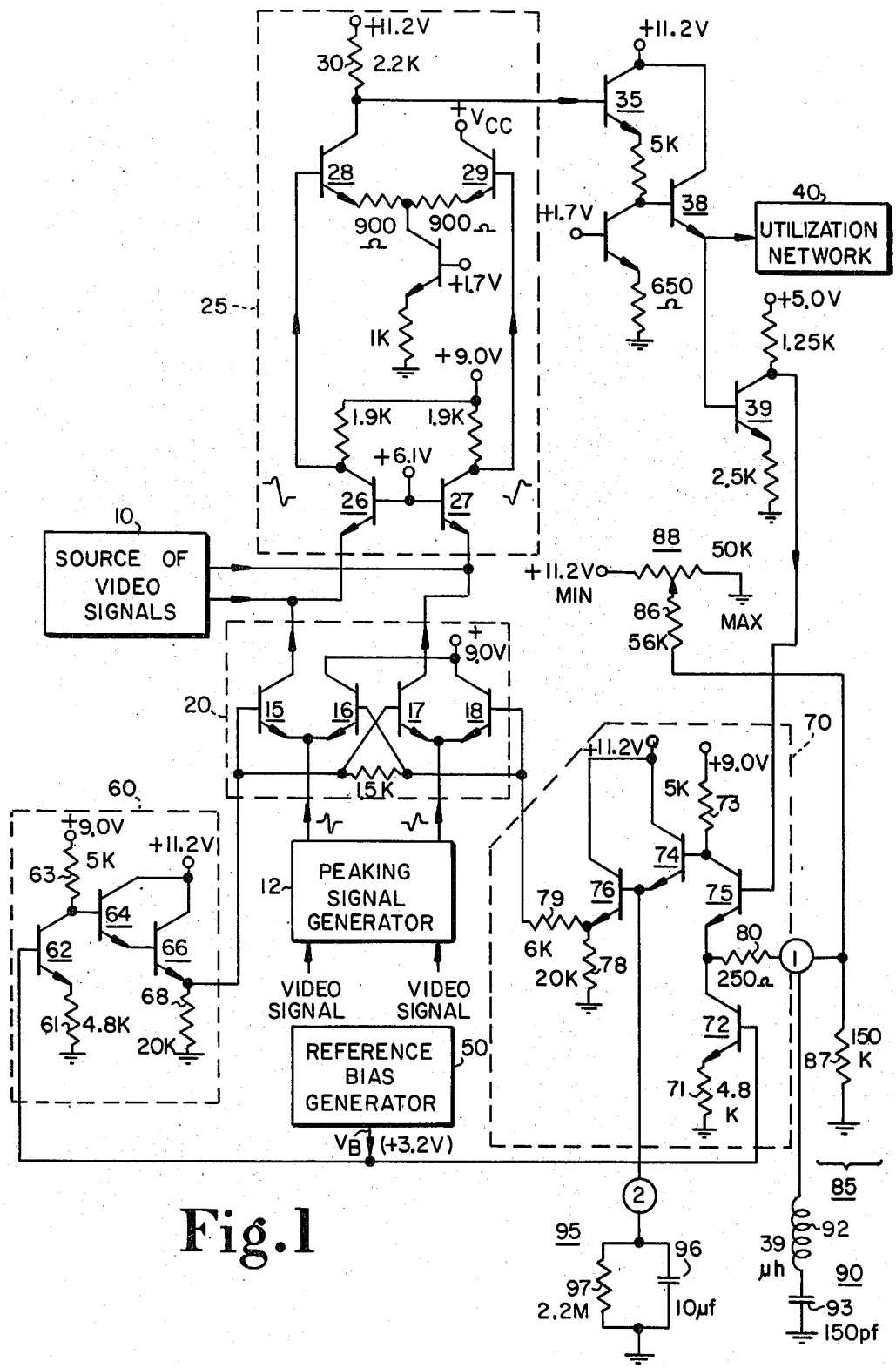
FIG. 1 shows a diagram, partially in block form and partially in schematic circuit form, of a portion of a television receiver including an embodiment of a control network according to the present invention.

In FIG. 1, complementary phased video signals are provided from a source 10. Complementary phased peaking signals are provided from a peaking signal generator 12 in response to the complementary phased video signals from source 10. Source 10 and signal generator 12 will be described in greater detail in connection with FIG. 2. The complementary phased peaking signals are DC coupled to respective inputs of a differentially controlled gate circuit 20, which operates as a signal splitter and comprises emitter coupled transistors 15, 16 and 17, 18. The complementary phased input peaking signals are respectively applied to the interconnected emitter inputs of transistors 15, 16 and 17, 18. The complementary phased video signals from source 10 are respectively DC coupled to the collector outputs of transistors 15 and 17 of gate 20, where the video signals are combined with the peaking signals to produce complementary phased peaked video signals. These signals are converted to a single phase peaked video signal by means of a network 25 comprising common base coupling transistors 26, 27 and a differential amplifier comprising transistors 28, 29. Specifically, the complementary phased peaked video signals are respectively coupled via emitter input transistors 26 and 27 to the differential base inputs of differentially connected transistors 28 and 29. The single phase peaked video signal is developed across a load resistor 30 and is DC coupled via emitter follower transistors 35 and 38 to a video signal utilization network 40. Network 40 includes appropriate signal processing stages for developing a video signal suitable for application to an image reproducing kinescope of the receiver.

Peaking signal gate 20 receives balanced quiescent bias derived from a DC reference bias voltage $V_B$, which is developed by a bias generator 50 and coupled to gate 20 via bias coupling networks 60 and 70. Bias coupling networks 60 and 70 are functionally symmetrical and provide balanced quiescent bias for differential control inputs of gate 20. Network 60 comprises an input transistor 62 with an emitter resistor 61 and a collector load resistor 63, followed by emitter follower transistors 64 and 66. A bias voltage (derived from voltage $V_B$) for one of the differential inputs of gate 20 is developed across an emitter resistor 68 of transistor 66. Network 70 comprises a DC input transistor 72 with an emitter resistor 71 and a load impedance comprising a transistor 75 and a resistor 73, followed by emitter follower transistors 74 and 76. The collector-emitter current paths of transistors 72 and 75 are arranged in series between first and second operating potentials (+9.0 volts and ground). A bias voltage (derived from voltage $V_B$) for the other differential input of gate 20 is developed across an emitter resistor 78 of transistor 76, and is applied to gate 20 via a resistor 79. The operation of the arrangement including gate 20 and bias networks 60 and 70 with respect to both quiescent and signal conditions will be described in greater detail subsequently.

Figure 2:
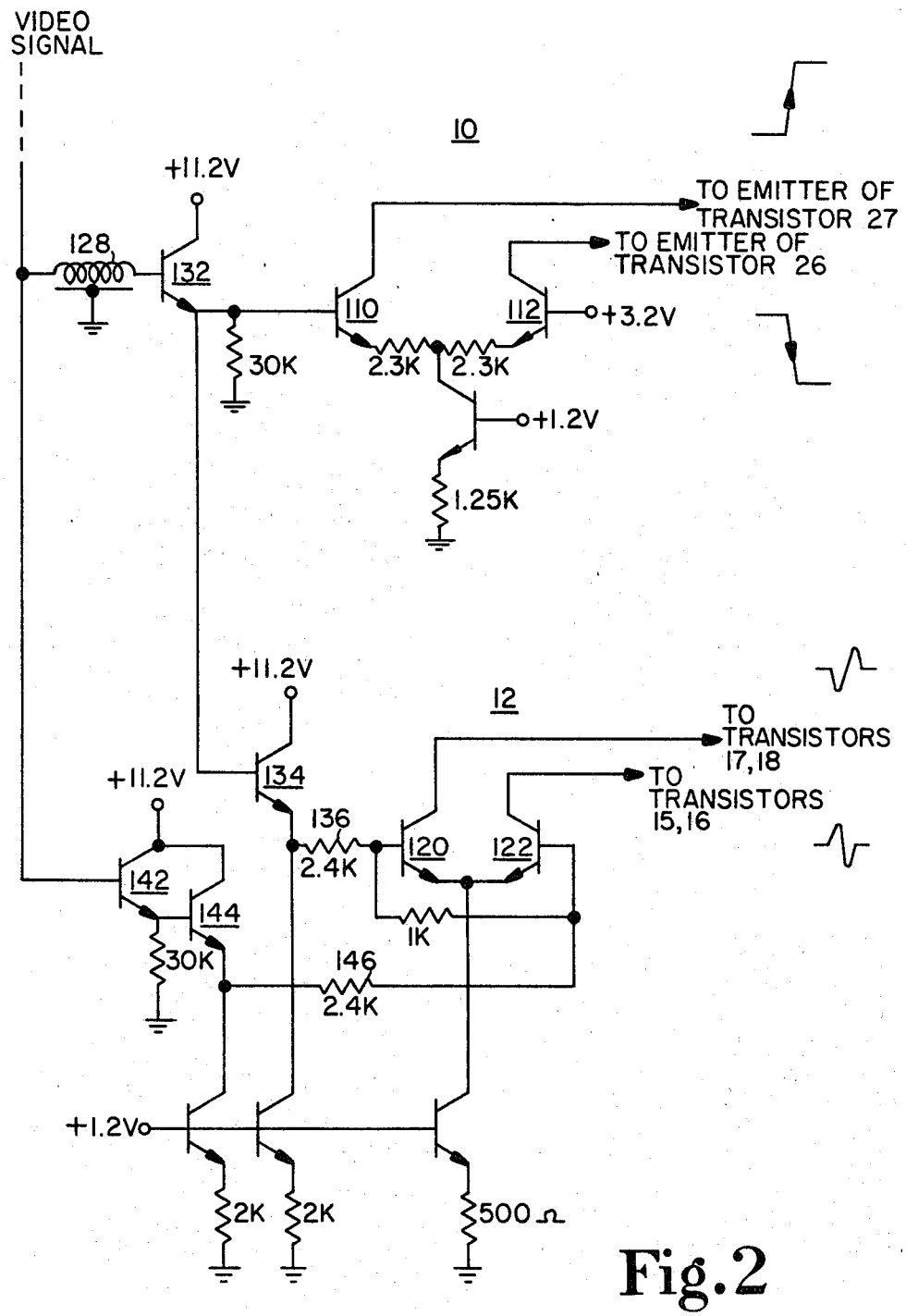
FIG. 2 shows additional details of portions of the arrangement of FIG. 1.

Before considering the peaking control operation of the system of FIG. 1, reference is made to FIG. 2 which shows additional details of video source 10 and peaking signal generator 12.

In FIG. 2, a wideband video signal (e.g., a luminance signal) with a bandwidth extending from DC to 4 MHz is applied to an input terminal of a delay line 128, and to one differential input of a differential amplifier comprising transistors 120 and 122 (included in peaking generator 12 shown in FIG. 1) via emitter follower transistors 142, 144 and a resistor 146. A delayed video signal from the output terminal of delay line 128 is coupled to another differential input of differential amplifier 120, 122 via emitter follower transistors 132, 134 and a resistor 136. Thus delay line 128 is coupled between the differential base inputs of transistors 120 and 122. The delayed video signal from the output terminal of delay line 128 is also coupled via follower transistor 132 to a differential amplifier comprising transistors 110 and 112 (included in video source 10 shown in FIG. 1). Differential amplifier 110, 112 develops complementary phased versions of the input wideband video signal, which respectively appear at the complementary phased collector outputs of transistors 110 and 112 and are DC coupled to the emitters of transistors 27 and 26 as shown in FIG. 1.

Delay line 128 is a wideband linear phase device throughout the video signal frequency range of approximately 4.0 MHz bandwidth. Delay line 128 provides a signal delay on the order of 140 nanoseconds such that the amplitude-versus-frequency response of the peaking signal generator has a peak amplitude response at approximately 1.8 MHz. More specifically, the response of the peaking signal generator resembles a sine-squared function wherein the signal peaking frequency ranges encompasses frequencies from 0.9 MHz to 2.7 MHz (the −6 db points), with a maximum amplitude response at 1.8 MHz. Since the output of delay line 128 is terminated by the high input impedance of transistor 132, the delay line output is essentially unterminated relative to its characteristic impedance whereby the delay line operated in a voltage reflective mode with a reflection coefficient of approximately unity. The input of delay line 128 is terminated in its characteristic impedance by means of a suitable terminating network.

A delayed video signal is developed at the base input of transistor 120. A video signal and a reflected and thus twice delayed video signal are summed at the base input of transistor 122. The signals developed at the base electrodes of transistors 120 and 122 cause differential amplifier 120, 122 to develop both preshoot and overshoot peaking signal components in the complementary phased collector circuits of transistors 120 and 122, as indicated by the signal waveforms. The complementary phased peaking signals appearing at the collectors of transistors 120 and 122 are coupled to transistors 15, 16 and 17, 18 shown in FIG. 1.

The operation of the automatic peaking control system will now be described with reference to FIG. 1.

The peaked wideband video signal developed at the emitter of transistor 38 and as supplied to utilization network 40 comprises high frequency information including peaking components which may be attributable to several sources, including the nature of the broadcast picture information, peaking provided at the transmitter, peaking provided in the receiver (e.g., via peaking generator 12), and noise, among other sources. The video signal also includes a DC component which varies with the picture information content of the video signal. A portion of the video signal from transistor 38 is DC coupled via a transistor 39 to video amplifier transistor 75 in network 70, to complete a DC coupled peaking control loop comprising network 70, peaking signal gate 20, signal coupling network 25, and transistors 35, 38 and 39.

Transistor 75 serves as a frequency selective signal amplifier for peaking control purposes, with a signal gain determined by the ratio of the collector impedance to the emitter impedance of transistor 75. The collector impedance of transistor 75 is primarily determined by the value of resistor 73. The emitter circuit of transistor 75 comprises transistor 72, a resistor 80, a bandpass filter network 90 coupled to a terminal 1, and a viewer adjustable peaking control network 85 also coupled to terminal 1. Network 85 comprises an adjustable voltage divider including a potentiometer 88 and large value resistors 86 and 87. As will be seen, within a given range of high frequencies the impedance between the emitter of transistor 75 and ground, and the gain of transistor 75, are primarily determined by the impedance of filter 90 and by resistor 80 for all settings of control potentiometer 88.

Filter 90 includes a series resonant combination of an inductor 92 and a capacitor 93, coupled between the emitter of transistor 75 and a point of reference potential (ground). Filter 90 exhibits a center frequency of approximately 2 MHz and a bandwidth of approximately 1 MHz. This frequency response determines the frequency response of transistor 75 and thereby the frequency response of the peaking control loop.

Filter 90 exhibits a relatively small impedance in response to signal frequencies between 1.5 MHz and 2.5 MHz, and a minimum impedance (essentially a short-circuit) in response to signals at the 2 MHz resonant frequency of filter 80. Thus within the bandwidth of filter 90 the impedance at the emitter of transistor 75 is then significantly less than the collector impedance of transistor 75. In such case the impedance at the emitter of transistor 75 corresponds to the sum of the impedance of filter 90 and the small value of resistor 80, since transistor 72 and network 88 each present a high impedance in shunt with the emitter of transistor 75. Thus transistor 75 exhibits significant gain at signal frequencies between 1.5 MHz and 2.5 MHz, corresponding to frequencies with which most of the video signal high frequency information including peaking components are associated, and exhibits a maximum gain at the 2 MHz resonant frequency of filter 90. The maximum gain can be conveniently adjusted by selecting an appropriate value of resistor 80. At lower video signal frequencies including DC, the impedance of filter 90 and thereby the emitter impedance of transistor 75 increase greatly, whereby the gain of transistor 75 decreases correspondingly and low frequency signals are greatly attentuated at the collector output of transistor 75. In particular, amplifier 75 exhibits a very small gain at DC, when filter 90 exhibits an extremely large maximum impedance (essentially an open circuit) due to the DC blocking action of capacitor 93. Accordingly, the arrangement of transistor 75 and peaking filter 90 represents an advantageous mechanism for suppressing low frequency video signal frequencies, and particularly DC components, in the DC coupled control path. High frequency signals above 3.0 MHz will also be attenuated by the selectivity of filter 90.

The high frequency signals passed by transistor 75 are detected by a peak detector stage comprising transistor 74 and a filter 95 including a capacitor 96 and a resistor 97. A DC control voltage developed on capacitor 96 is proportional to the amount of high frequency present in the video signal, including peaking components. This control voltage is applied via follower transistor 76 and resistor 79 to input control transistors 16 and 18 of gate 20 for controlling the amount of peaking signal which is conducted from generator 12 to the video signal from source 10. The amount of peaking imparted to the video signal is therefore maintained within desired limits, consistent with the setting of adjustable peaking control potentiometer 88 in network 85. As will be discussed, the amount of peaking imparted to the video signal can be adjusted manually by means of peaking control 88, which serves to control the amount of current conducted by transistor 75 and thereby modifies the control voltage developed on capacitor 96. As a practical matter, the typical frequency response of an overall television receiver system and the frequency content of normally experienced video signals are such that the described frequency response of the peaking control system, as determined by filter 90, provides a suitable indication of video signal high frequency information including peaking components. However, other system frequency responses are also possible, depending on the requirements of a particular system.

The peaking control system as so far described exhibits several significant features which facilitate the construction of the system in an integrated circuit in large part. In such case, terminals 1 and 2 correspond to external terminals of the integrated circuit, and adjustable peaking control network 85, bandpass filter 90, and peak detector filter 95 correspond to discrete circuits situated external to the integrated circuit.

The peaking control system is DC coupled and predictably biased by employing balanced, symmetrical quiescent bias networks and complementary phased signal coupling networks. Specifically, complementary phase peaking signals from generator 12 are combined with complementary phase video signals from source 10 to produce complementary phase peaked video signals, which are differentially combined in differential amplifier 28, 29 to produce a signal phased peaked video signal. In addition, bias coupling networks 60 and 70 are arranged to provide symmetrical, balanced quiescent voltages (as derived from bias reference voltage $V_B$) to peaking control gate 20 via the emitters of transistors 66 and 76. In this regard it is noted that, for a nominal center setting of adjustable peaking control 88, the quiescent voltages developed at the collectors of transistors 75 and 62 are substantially equal, and the quiescent emitter voltages of transistors 66 and 76 are also substantially equal. These voltages vary from mutual equality as control 88 is adjusted about the center position, whereby gate 20 is caused to provide a controlled amount of output peaking signal consistent with the position of control 88.

Bias coupling networks 60 and 70 are functionally symmetrical, and are structurally symmetrical with two exceptions which do not compromise the intended balanced quiescent bias coupling action of these networks. First, bias voltage $V_B$ is applied to an input transistor 62 in network 60, but to an input cascade combination of DC input transistor 72 and transistor 75 in network 70. However, assuming control 88 is centered, the quiescent collector voltages of transistors 62 and 75 in response to voltage $V_B$ are substantially equal since the quiescent collector currents conducted by transistors 72 and 75 are substantially equal and are equal to the quiescent collector current of transistor 62 in network 60. Second, resistor 79 does not upset the desired balanced bias coupling to the differential control inputs of gate 20, since the quiescent voltage drop across resistor 79 is a function of the negligibly small input (base) currents of the input transistors of gate 20. Resistor 79 is not required in all cases, and assists to achieve gate control voltage bias predictability in conjunction with control network 88, particularly when the peaking control network including network 70 is constructed as an integrated circuit and network 85 is situated external to the integrated circuit.

As a result of the described symmetrical quiescent biasing of gate 20, and as a result of the described complementary phase signal coupling and differential combining, the arrangement of gate 20 and signal coupling and combining network 25 is substantially insensitive to common mode effects (e.g., operating supply variations, variations in the level of bias voltage $V_B$, and temperature effects) which could otherwise adversely affect the operation of the system. This result is advantageous when, as in this case, differentially controlled gate 20 operates in response to a small differential control voltage range of about 200 millivolts, as developed between the base electrodes of transistors 16 and 17. Thus it is important to prevent even a small quiescent bias offset error in the differential control voltage, to preserve the desired peaking control capability of gate 20 in response to the control voltage developed on capacitor 96.

The DC coupled arrangement of bias coupling network 70 including peak detector transistor 74 simultaneously establishes the proper quiescent bias of detector transistor 74, and the desired balanced bias to the differential control inputs of gate 20 in conjunction with bias coupling network 60. With this arrangement the proper quiescent bias of detector transistor 74 is established predictably and automatically without disturbing the desired balanced quiescent bias provided to the differential control inputs of gate 20. Thus it is not necessary to establish the quiescent bias of detector transistor 74 by other means, e.g., an independent bias network, which could increase the likelihood of the detected output voltage from transistor 74, and thereby the control of gate 20, being undesirably influenced by factors such as bias supply variations and temperature effects if additional compensating measures are not taken.

The combination of cascode connected transistors 72 and 75 with filter 90 represents an advantageous means for shaping the frequency response of the DC coupled peaking control loop, particularly with respect to suppressing DC components in the video signal coupled to detector transistor 74 via transistor 75. The DC component of the video signal varies with the picture information content of the video signal, and would undesirably distort or obscure the control voltage developed on capacitor 96.

Transistor 72 represents a source of substantially constant quiescent current for amplifier transistor 75. Since the collector impedance of transistor 72 is extremely high, transistor 72 has no effect on the operation of filter network 90 or on the operation of adjustable peaking control network 85. There is no shunting effect produced at the emitter control input of transistor 75 with respect to the operation of these networks. Conversely, the quiescent current supplied by transistor 72 is unaffected by filter 90 or by adjustment of peaking control network 85. Thus, for any setting of peaking control potentiometer 88, the arrangement of cascode transistors 72 and 75 with filter 90 permits amplifier transistor 75 to exhibit a predictable gain variation from a maximum at 2 MHz to a minimum at DC.

The gain of amplifier 75 is very small at DC, as determined by the highly degenerative high impedance presented to the emitter of transistor 75. To illustrate the effectiveness of the arrangement of cascode transistors 72, 75 and filter 90 for suppressing video signal DC components in the control path preceding detector 74, 95, it is noted that in the absence of adjustable network 85 the gain of amplifier 75 at DC approaches an extremely small value since the emitter impedance of transistor 75 is then determined by the extremely high collector impedance of transistor 72 (on the order of several hundred kilohms to megohm), and by the circuit impedance of filter 90 which at DC is an open circuit due to the DC blocking action of capacitor 93. In this instance the ratio of the collector to emitter impedance of transistor 75, which determines the gain of transistor 75, is an extremely small number.

To further illustrate this concept of video signal DC suppression in the control path, assume that video signals from source 10 are absent. The system will then exhibit a quiescent condition whereby a quiescent DC bias appears at the base of transistor 75, and the differential control inputs of gate 20 receive proper quiescent bias via bias coupling networks 60 and 70 in accordance with the setting of potentiometer 88. Now assume that video signals with a DC component are present. This DC component will appear at the base of amplifier transistor 75 and will modify the base bias of transistor 75 relative to its quiescent base bias. However, the current conduction of transistor 75 will remain substantially unchanged in response to the DC component of the video signal due to the extremely high collector impedance of constant current source transistor 72 and the DC open circuit condition of filter 90. Accordingly, the collector voltage of amplifier transistor 75 and thereby the voltage on detector capacitor 96 remain substantially unchanged in response to the video signal DC component. The high equivalent impedance presented by adjustable peaking control network 85 renders transistor 75 only slightly less insensitive to the video signal DC component, but does not compromise the effectiveness of the control system as a practical matter.

Adjustment of peaking control 88 varies the DC current conducted by amplifier transistor 75 by adding and subtracting DC current to and from the emitter current of transistor 75. Peaking control 88 can be adjusted without impairing the operation of filter 90 for signals within its passband, since the high impedance of network 85 is significantly greater then the impedance of filter 90 at high frequencies. Conversely, filter 90 does nto affect the adjustable peaking control DC bias provided from network 85 to the control path via terminal 1, since capacitor 93 of filter 90 acts as a DC blocking capacitor whereby filter 90 exhibits a very high impedance between terminal 1 and ground for DC. Thus filter 90 and adjustable control network 85 exhibit mutually independent operation with respect to control of amplifier 75, although filter 90 and control network 85 are connected to the same, single terminal.

The fact that filter 90 and adjustable peaking control network 85 are connected to the same single terminal is particularly advantageous when the peaking control system is constructed as an integrated circuit wherein terminal 1 corresponds to an external terminal of the integrated circuit, since such connection results in conserving the limited number of external integrated circuit terminals.

Continuing now with the operation of the system, the automatic peaking control loop is closed (i.e. operative) as a function of the amount of high frequency content in the video signal and the setting of control 88. Illustratively, assuming that the high frequency content of the video signal is substantially constant, and that peaking control 88 is set at an approximately mid-range position, an equilibrium condition will result with respect to the voltage on capacitor 96, the control voltage applied to peaking gate 20, and the amount of peaking signal coupled by network 20 from peaking generator 12 to the video signal. The closed control loop will act to maintain this desired level of peaking, consistent with the setting of peaking control 88 and the corresponding bias supplied to transistor 75 via control 88, in the presence of a change in the video signal high frequency content.

For example, an increase in the high frequency content of the video signal produces a corresponding increase in the voltage on capacitor 96 and at the emitter of transistor 76, which in turn causes the conduction of transistors 16 and 18 of gate 20 to increase. These transistors accordingly conduct more of the peaking signal from generator 12. Due to the signal splitting action of gate 20, transistors 15 and 17 conduct correspondingly less of the peaking signal, and less peaking signal is added to the video signal at the collectors of transistors 15 and 17. The peaking content of the video signal supplied to utilization network 40 is therefore reduced to the desired level. At this time the control loop exhibits a new equilibrium condition, which remains until the control loop again reacts in response to a change in the video signal high frequency content, or until peaking control 88 is adjusted by the viewer. Observations analogous to the above also apply when the control loop acts to automatically increase the amount of peaking.

The combination of the setting of peaking control 88 and the high frequency content of the video signal can result in a condition wherein no peaking signals from generator 12 are added to the video signal from source 10. In such case the control voltage at the emitter of transistor 76 is sufficiently large (positive) so that transistors 16 and 18 of gate 20 conduct all of the peaking signal from generator 12.

Figure 3:
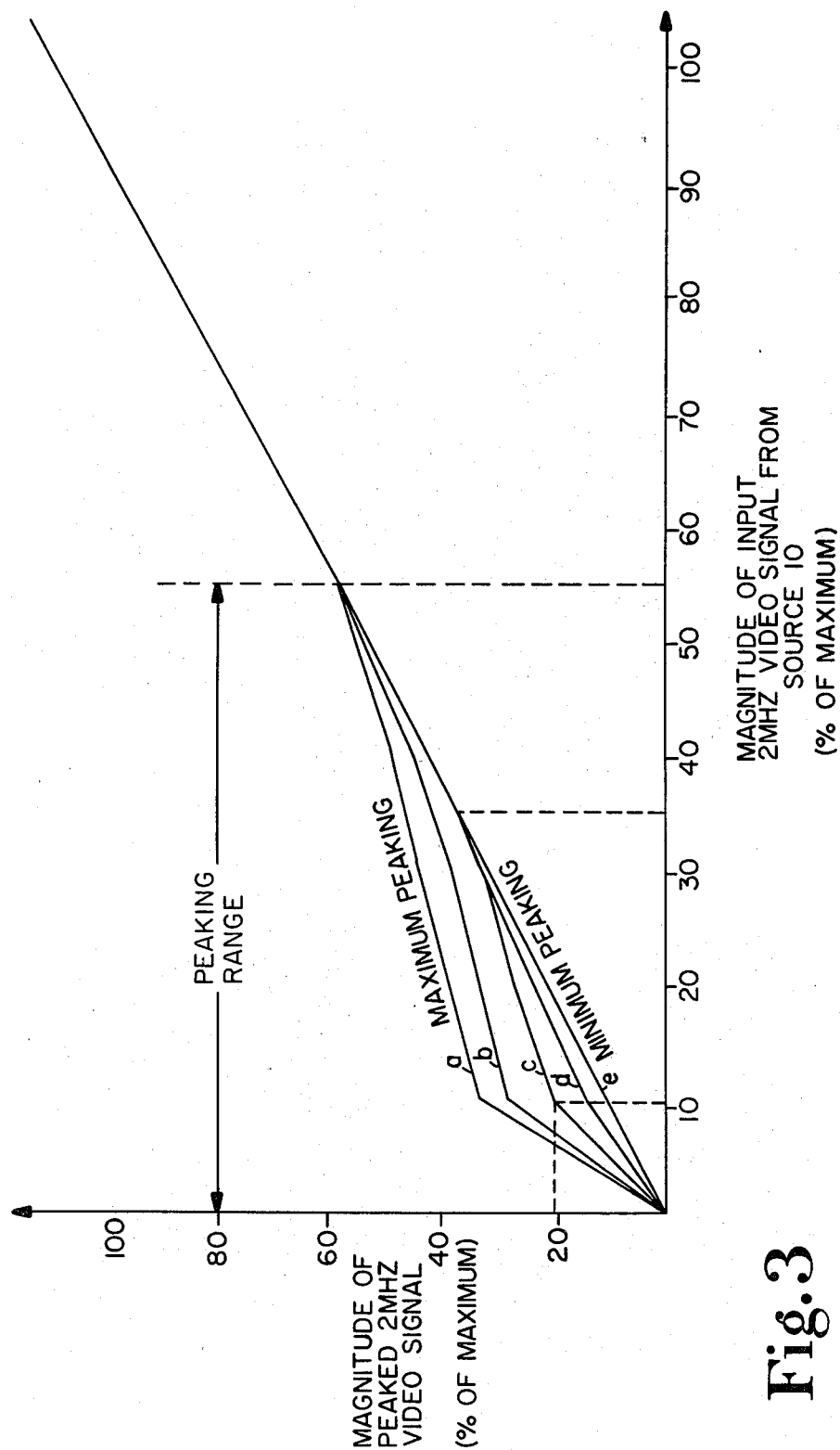
FIG. 3 illustrates the response of the control network shown in FIG. 1.

FIG. 3 illustrates the operation of the peaking control loop in response to the setting of peaking control 88 and the video signal high frequency content. For purposes of this illustration it is assumed that the video signal from source 10 consists of a high frequency 2 MHz signal.

In FIG. 3, the horizontal axis represents the increasing magnitude of the input 2 MHz video signal from source 10, between zero and 100% of the normally expected magnitude of the video signal. The vertical axis represents the corresponding magnitude of the 2 MHz video signal after additional peaking signals from generator 12 have been selectively added to the video signal. The five peaking responses shown, labeled "a" through "e", respectively correspond to maximum through minimum peaking settings of peaking control 88. In this system peaking control operates over a range of video signal magnitudes from zero to approximately 55% of the maximum expected video signal magnitude.

When control 88 is set to minimum peaking position "e", no peaking signal is added to the input 2 MHz video signal. Peaking signals are added to the input video signal over the entire peaking range when peaking control 88 is set to maximum peaking position "a". At intermediate setting "c", for example, the amount of peaking added to the video signal substantially equals the magnitude of the input video signal when the input video signal is between zero and 10% of maximum. For this setting no peaking is added to the video signal when the video signal strength exceeds approximately 35% of maximum.

Referring now to FIG. 2 together with FIG. 1, it is seen that transistors 120 and 122 (FIG. 2) from which the peaking signals are provided, form a cascode signal coupling configuration with transistors 17, 18 and 15, 16 of current splitter gate 20 (FIG. 1), respectively. This cascode arrangement in conjunction with the current splitting action of gate 20 significantly reduces the likelihood of distortion and phase error in the peaking signals that are combined with the video signals from source 10. The cascode coupling configuration significantly reduces high frequency feedback which would otherwise produce high frequency distortion. In addition, a substantially constant low impedance is presented by the emitters of transistors 15, 16 and 17, 18 of gate 20 to the collector outputs of transistors 122 and 120 of the peaking signal generator as gate 20 is controlled (i.e., as the conduction of transistors 15–18 is varied). As a result, phase shift errors in the peaking signals, due to the effects of parasitic capacitances, are significantly reduced.

Automatic peaking control by means of controlling the amount of peaking signal combined with the wideband video signal from source 10 is advantageous in that this manner of control does not disturb the signal processing parameters of the wideband video signal path including delay line 128 and differential amplifier 110, 112 as shown in FIG. 2. In particular, the phase of the wideband video signals subjected to peaking is not affected as the amount of peaking imparted to the video signal is controlled.

What is claimed is:

1. Apparatus for automatically and manually controlling the high frequency peaking content of a video signal, comprising:
   peaking means responsive to said video signal for generating an output peaking component, said peaking means providing controllable amount of said output peaking component in response to a peaking control voltage;
   means for combining said video signal with said peaking component to produce a peaked video signal;
   control means responsive to said video signal and providing said peaking control voltage to said peaking means;
   filter means coupled to said control means for shaping the frequency response of said control means such that, in an automatic peaking control mode, said control voltage is a function of the magnitude of video signal high frequency components within a given frequency range; and
   manually adjustable peaking control means coupled to said control means for controlling the conduction of said control means such that, in a manual peaking control mode, said control voltage is a function of the setting of said manually adjustable peaking control means; and wherein
   said filter means and said manually adjustable peaking control means are interconnected and coupled to said control means via a single common terminal.

2. Apparatus according to claim 1, wherein
   said control means is constructed in an integrated circuit;
   said terminal corresponds to a single external terminal of said integrated circuit; and
   said filter means and said manually adjustable peaking means are situated external to said integrated circuit.

3. Apparatus according to claim 2, wherein
   said control means responds to said peaked video signal.

4. Apparatus according to claim 1 or 2, wherein said control means comprises:
   a transistor with a first electrode for receiving said video signal, a second electrode coupled to said peaking means, and a third electrode; said third electrode being common to current paths consisting of a first current path including a source of substantially constant quiescent operating current for said transistor, and a second current path including said terminal.

5. Apparatus according to claim 4, wherein said second current path comprises:
   an AC coupled current path between said terminal and a point of reference potential, including said filter means; and
   a DC coupled current path between said terminal and a point of reference potential, including said manually adjustable peaking control means; and wherein
   said manually adjustable peaking control means exhibits a high impedance relative to the impedance exhibited by said filter means at signal frequencies within said given frequency range.

6. Apparatus for automatically and manually controlling the high frequency peaking content of a video signal, comprising:
   peaking means responsive to said video signal for generating an output peaking component, said peaking means providing controllable amount of said output peaking component in response to a control voltage;
   means for combining said video signal with said peaking component to produce a peaked video signal;
   charge storage means;
   control means with an input for receiving said video signal and an output coupled to said peaking means, said control means being constructed in an integrated circuit and coupled to an external terminal of said integrated circuit, said control means comprising
   an amplifier with an input for receiving said video signal, and an output;
   a detector with an input for receiving output signals from said amplifier and an output coupled to said charge storage means for producing a control voltage representative of the magnitude of output signals from said amplifier; and means for coupling said control voltage to said peaking means for controlling the magnitude of said peaking component and thereby controlling the peaking content of said peaked video signal;

filter means coupled to said amplifier for shaping the frequency response of said amplifier such that, in an automatic peaking control mode, said control voltage is a function of video signal high frequency components within a given frequency range; and manually adjustable peaking control means coupled to said amplifier for controlling the conduction of said amplifier such that, in a manual peaking control mode, said control voltage is a function of the setting of said manually adjustable peaking control means; and wherein said filter means and said manually adjustable peaking control means are situated external to said integrated circuit and are coupled to said integrated circuit via said external terminal of said integrated circuit.

7. Apparatus according to claim 6, wherein said amplifier receives said peaked video signal.

8. Apparatus according to claim 6, wherein said amplifier comprises an amplifier transistor and a current source transistor with respective main current conduction paths coupled in series, said amplifier transistor having a signal input responsive to said video signal, a low impedance bias control input, and an output coupled to a load impedance; said current source transistor being coupled to said bias control input of said amplifier transistor for providing quiescent operating current for said amplifier transistor;

said filter means includes a capacitor and is AC coupled between said low impedance bias control input of said amplifier transistor and a point of reference potential, said filter means being tuned to exhibit a first impedance at DC such that said amplifier transistor exhibits a first gain at DC, and a significantly smaller second impedance at a frequency within said given frequency range such that said amplifier transistor then exhibits a second gain significantly greater than said first gain; and said manually adjustable peaking control means exhibits a high impedance relative to said second impedance exhibited by said filter means.

9. Apparatus according to claim 8, wherein said current source transistor provides a substantially constant quiescent operating current.

10. Apparatus according to claim 8, wherein said amplifier comprises a load impedance;

an amplifier transistor with a base input for receiving said video signal, a collector output coupled to said load impedance, and an emitter bias control input; and a current source transistor with a collector output coupled to said emitter of said amplifier transistor for supplying a substantially constant quiescent operating current to said amplifier transistor;

said filter means comprises a series resonant bandpass filter including a capacitor and is coupled between said emitter of said amplifier transistor and a point of reference potential, said filter being tuned to exhibit a first impedance at DC such that said amplifier transistor exhibits a first gain at DC, and a significantly smaller second impedance at a frequency within said given frequency range such that said amplifier transistor then exhibits a second gain significantly greater than said first gain; and said manually adjustable peaking control means comprises a potentiometer and exhibits a high impedance relative to said second impedance exhibited by said filter, for all settings of said potentiometer.

11. Apparatus according to claim 10, wherein said filter comprises the series combination of an inductor and a capacitor.

12. Apparatus for generating a D.C. control signal for controlling the operation of an electrical circuit, said apparatus comprising:

frequency selective direct current coupled amplifier means for amplifying a predetermined frequency component of an input alternating current signal;

means for detecting the magnitude of amplified frequency components from said amplifier means to generate said D.C. control signal in accordance with the detected magnitude of said amplified frequency component;

manually adjustable means for generating a variable D.C. input signal;

filter means for determining the frequency response of said amplifier means;

a terminal to which said manually adjustable means and said filter means are connected; and means connecting said terminal to said direct current coupled amplifier means for coupling said variable D.C. input signal to said detecting means via said amplifier means such that said variable D.C. input signal varies said D.C. control signal substantially without varying the signal gain of said amplifier means.

* * * * *